United States Patent [19]

Salomé

[11] Patent Number: 5,536,651

[45] Date of Patent: * Jul. 16, 1996

[54] **MUTANT STRAIN OF *XANTHOMONAS CAMPESTRIS*, PROCESS OF OBTAINING XANTHAN, AND NON-VISCOUS XANTHAN**

[75] Inventor: Marc Salomé, Castanet-Tolosan, France

[73] Assignees: Sanofi, Paris; Societe Nationale Elf Aguitaine, Courbevoie, both of France

[*] Notice: The term of this patent shall not extend beyond the expiration date of Pat. No. 5,401,644.

[21] Appl. No.: 404,323

[22] Filed: Mar. 15, 1995

Related U.S. Application Data

[62] Division of Ser. No. 813,838, Dec. 27, 1991, Pat. No. 5,401,644.

[30] Foreign Application Priority Data

Dec. 28, 1990 [FR] France ................................. 90 16515

[51] Int. Cl.$^6$ ........................... C12P 19/06; C12P 19/12; C12N 1/00; C07G 17/00
[52] U.S. Cl. ........................ 435/104; 435/100; 435/910; 435/243; 435/252.1; 536/114; 536/124
[58] Field of Search ..................................... 435/104, 100, 435/252.3, 910, 243, 252.1; 536/114, 124

[56] References Cited

U.S. PATENT DOCUMENTS

| | | | |
|---|---|---|---|
| 4,352,882 | 10/1982 | Maury | 435/104 |
| 4,357,260 | 11/1982 | Sandford et al. | 435/104 |
| 4,377,637 | 3/1983 | Weisrock | 435/104 |
| 4,692,408 | 9/1987 | Banks et al. | 435/104 |
| 4,696,900 | 9/1987 | Ellwood et al. | 435/104 |
| 5,003,060 | 3/1991 | Vinot | 536/114 |
| 5,017,479 | 5/1991 | Eyssautier | 435/104 |
| 5,279,961 | 1/1994 | Pollock et al. | 435/104 |
| 5,340,743 | 8/1994 | Pollock et al. | 435/104 |
| 5,401,644 | 3/1995 | Salomé | 435/104 |

*Primary Examiner*—Douglas W. Robinson
*Assistant Examiner*—Louise N. Leary
*Attorney, Agent, or Firm*—Foley & Lardner

[57] ABSTRACT

The present invention relates to
- a mutant strain of *Xanthomonas campestris*;
- a method of preparing xanthan by fermentation of said strain; and
- a non-viscous xanthan capable of being obtained by said method.

17 Claims, No Drawings

MUTANT STRAIN OF *XANTHOMONAS CAMPESTRIS*, PROCESS OF OBTAINING XANTHAN, AND NON-VISCOUS XANTHAN

This application is a division of application Ser. No. 07/813,838, filed Dec. 27, 1991, now U.S. Pat. No. 5,401,644.

The present invention relates to a mutant strain of *Xanthomonas campestris*, to a method of fermenting this microorganism to give xanthan, and to a non-viscous xanthan capable of being produced by said method.

The viscosity of aqueous solutions of xanthan has led to the use of this polysaccharide as a thickener and stabilizer of suspensions in the food, cosmetic and pharmaceutical industries, in paints and inks and for enhanced recovery of petroleum.

Xanthan is a polymer whose backbone, which has the same structure as that of cellulose, carries trisaccharidic pendant groups substituted by acetate or pyruvate groups. It is known that, depending on the producing strains and the culture conditions, the polysaccharide produced can have more or less substantially modified side units and a variable, although always very high, average molecular weight. This can cause variations in its physical properties, especially its viscosity; nevertheless, no polysaccharide having the xanthan structure has ever been isolated whose aqueous solutions have a practically unmeasurable viscosity.

It has now been found that a new strain of *Xanthomonas campestris* gives a very low viscosity xanthan under good productivity conditions.

According to a first feature, the invention relates to the strain of *Xanthomonas campestris* deposited in the Collection Nationale de Culture de Microorganismes (CNCM) Institut Pasteur 28, rue du Dr Roux 75724 Paris Cedex 15 France on 15 Jun. 1990, under n° I-956, in accordance with the treaty of Budapest.

This mutant strain was selected on a liquid medium containing inorganic nitrogen as the only nitrogen source and glycerol as the only carbon source. It can be cultivated in a synthetic liquid medium and on a solid medium.

The microorganism takes the form of rods and its yellow and mucous colonies on a solid medium, in the presence of glucose, do not differ from those of the parent strain NRRL B-1459.

The mutant strain is distinguished by its rapid growth on glycerol as the only carbon source, by comparison with the parent strain NRRL B-1459 and with the strain ATCC 31600, which is capable of growing on a synthetic medium; it is resistant to streptomycin and nalidixic acid and does not assimilate lactose.

According to another feature, the invention relates to a process of fermenting this microorganism for the production of conventional or non-viscous xanthan. The production phase of this process has to take place in the presence of calcium ions and of an alkali metal hexametaphosphate, preferably sodium hexametaphosphate.

The medium used during the growth phase of the mutant strain—the multiplication phase of the microorganism—preferably contains glycerol as the only carbon source; the other components of said medium are those normally encountered in Xanthomonas fermentations, which those skilled in the art will choose, with the help of a few preliminary experiments, in order to give optimum growth. Thus salts providing phosphate, magnesium, potassium and sulfur, as well as iron, calcium and trace elements, will be added to a nitrogen source which can be inorganic, such as an ammonium salt or more complex.

A buffer mixture which will fix the pH at about 7, comprising for example 3-morpholinopropanesulfonic acid, may also be incorporated in the medium.

Glycerol is assimilated rapidly by the mutant strain, including in the presence of a mixture of amino acids. In the absence of another carbon source, the unnecessary and troublesome production of xanthan is suppressed during this first phase.

A suitable nitrogen source will consist of a mixture of casein hydrolyzate, glutamic acid and yeast extract. Furthermore, the presence of boron among the trace elements favors the growth of the microorganism. The diluent for the growth medium is water, which is deionized so as not to interfere with the ions introduced.

The medium intended for the production phase of conventional or non-viscous xanthan by the strain of the invention contains: a conventional carbon source, such as a saccharide, which, with an ordinary strain, would lead to the production of viscous xanthan; one or more nitrogen sources; and salts providing the ions normally found in fermentations of this type, such as phosphate, magnesium, potassium and sulfur, as well as iron, calcium and a solution of trace elements.

In addition, this is a characteristic of the process of the present invention, the production medium contains an alkali metal hexametaphosphate at an initial concentration of between 50 and 500 mg/l and preferably of between 200 and 300 mg/l, which requires the presence of 1 mg to 15 mg of $Ca^{++}$/l.

The alkali metal hexametaphosphate is advantageously sodium hexametaphosphate.

The diluent for the production medium is deionized water.

The carbon source is preferably fructose and more preferably glucose; the nitrogen source is preferably lysine, by itself or mixed with a casein hydrolyzate.

For the production, according to the invention, of a non-viscous xanthan, the cultivation medium must remain non-viscous and so easy to agitate and aerate throughout the fermentation, and the fermentation must be stopped as soon as the viscosity of the medium starts to increase; in fact, if the fermentation is continued, conventional xanthan gradually appears in the medium and it is possible, after a prolonged fermentation, to obtain only xanthan having usual viscosity. However, the addition of an alkali metal hexametaphosphate in an amount of 50 to 200 mg/l of medium, and preferably of about 100 mg/l, as soon as the viscosity starts to increase enables the viscosity increase to be halted and the production of non-viscous xanthan to be prolonged.

It is also suitable to add in this case sodium hexametaphosphate.

In general, the fermentation time is about 30 hours before viscosity is seen to appear in the fermentation broth, but the fermentation can be continued for 10 hours or more with hexametaphosphate being added to the medium.

The fermentation can be stopped at any time before viscosity appears, but it is preferable to wait until practically all the carbon source has been consumed.

As the medium at the end of fermentation is not viscous, separation of the cellular substances and any insoluble materials from dissolved xanthan is easy by centrifugation, microfiltration or ultrafiltration; in this last case, the cells can be recycled and the fermentation resumed after simply adding the components necessary for the production phase to the medium in which the cells remained in suspension.

The resulting polysaccharide solutions are clear and can be used as such in certain domains.

The polysaccharide can also be isolated, before or after separation of the insoluble materials, by a known method of precipitation: a water-miscible solvent in which the polysaccharide is insoluble, such as acetone, ethanol or, preferably, isopropanol, is added to the medium; as for a conventional fermentation, the presence of low concentrations of alkali metal or alkaline earth metal ions, especially calcium ions, from 50 to 100 mM, in the medium improves the precipitation.

For certain uses, for example in cosmetics, it may be desirable to isolate a xanthan which is free of lipopolysaccharides, the pyrogenic activity of which is well known. It is known that, as Xanthomonas are Gram-bacteria, substantial amounts of lipopolysaccharides are released into the fermentation medium; they may be removed by precipitation, before precipitation of the non-viscous polysaccharide, by known techniques such as the addition of alkaline earth metal ions in a basic medium.

For the production, according to another aspect of the invention, of conventional viscous xanthan, the strain of Xanthomonas of the invention is cultivated in a production medium containing an alkali metal hexametaphosphate at a concentration from 50 mg/l to 500 mg/l, and preferably from 200 to 300 mg/l, and calcium ions in an amount of 1 to 15 mg of $Ca^{++}/l$, and the fermentation is carried on until the viscosity of the medium is comparable to that of a conventional production medium before the xanthan is isolated by known methods. The further addition of an alkali metal hexametaphosphate in an amount of 50 to 200 mg/l medium, and preferably of about 100 mg/l as soon as the viscosity starts to increase is not excluded in said production of conventional viscous xanthan.

Such a process is advantageous insofar as the production medium is viscous for an appreciably shorter time than in a conventional fermentation with the same productivity. The consumption of agitation energy is thus markedly reduced.

The production medium for obtaining viscous or non-viscous xanthan has the same characteristics, namely the presence of an alkali metal hexametaphosphate—preferably sodium hexametaphosphate—and calcium ions.

According to a last aspect, the invention relates to a new non-viscous xanthan.

Non-viscous xanthan is understood as meaning a product whose aqueous solutions at a concentration of 10 g/l, containing about 1% (w/v) of KCl, have a viscosity of less than 700 mPa.s and preferably of less than 250 mPa.s, measured using a Brookfield model LVT viscometer equipped with a n° 1 or 2 spindle rotating at 60 rpm, at 25° C., whereas the viscosity of the known xanthans is between 1200 and 1500 mPa.s. This viscosity measurement is carried out in conventional manner in the presence of KCl so as to give a result independent of the amount of ions which can be introduced into the water with the xanthan to be studied.

The chemical composition of this non-viscous xanthan is identical to that of the known xanthans, in particular as regards the acetate and pyruvate groups; by contrast, the average molecular weight of the polymer is less than that of viscous xanthans.

With a method coupling exclusion chromatography with low angle laser light scattering, described for example in Carbohydrate Polymers 6, p. 477–492 (1986), it was determined that the molecular weights of commercially available xanthans were $2\times10^6$ or more, whereas the average molecular weight of the non-viscous polysaccharide according to the invention is of the order of 6 to $7\times10^5$.

Solutions of the non-viscous xanthan according to the invention at concentrations of 1 to 20 g/l do not become viscous on heating at from 80° C. to 120° C. for 5 to 30 minutes.

A non-viscous xanthan having these structural characteristics has never been described and the invention is not limited to the polysaccharide produced by the strain CNCM I-956; it also relates to non-viscous polysaccharides which have the chemical structure of xanthan and which could be produced by different mutant strain of Xanthomonas campestris or by microorganism of a different species or genus, which may have been obtained by genetic engineering, these could be prepared by chemical synthesis or semisynthesis, also.

The non-viscous xanthan according to the invention can be used for its suspending property. For the classical uses of conventional xanthan, based on viscosity-enhancing and thickening properties, it is avantageous to mix it with a conventional viscous xanthan to give xanthan compositions of intermediate viscosities and reproducible properties, which nevertheless have the valuable theological characteristics of xanthan, i.e. invariable viscosity of its solutions over wide temperature and pH ranges and pseudoplasticity.

Like the non-viscous xanthan according to the invention, these xanthan compositions can be associated with other polysaccharides, such as carrageenans, pectins, gelatins, alginates, especially in the food industry.

Moreover, the non-viscous xanthan may be used for its film-forming property, for instance in baking.

The non-viscous xanthan according to the invention may be subjected to chemical reactions more easily than a viscous xanthan to give useful products by grafting or crosslinking.

Examples of how to carry out the invention are described below.

EXAMPLE 1

Preparation of non-viscous xanthan in a laboratory fermentor

The mutant Xanthomonas campestris strain CNCM I-956 can be preserved in conventional manner, either lyophilized or in a tube frozen at −80° C. in an aqueous medium containing 20% of glycerol.

a) Growth phase

The growth medium is prepared beforehand:

The following are dissolved in 800 ml of deionized water: $FeSO_4.7H_2O$ (0.125 g); $CaCl_2.2H_2O$ (0.015 g); $MgSO_4.7H_2O$ (0.300 g); $K_2SO_4$ (0.040 g); NaCl (0.125 g); glutamic acid (3.0 g); yeast extract (1.0 g); and casein hydrolyzate (7.5 g), and a solution of trace elements (1 ml) is added.

The casein hydrolyzate is, for example, that marketed by HUMKO SHEFFIELD (USA) under the name "Hy-Case, salt free"; the solution of trace elements is prepared by dissolving the following in 900 ml of deionized water: 10 g of $MnCl_2$, 2 g of $ZnSO_4.7H_2O$, 25 mg of $CuSO_4.5H_2O$, 2 g of $CoCl_2.6H_2O$, 0.5 g of $H_3BO_3$, 180 mg of KI, 1.9 g of $Na_2MoO_4.2H_2O$, 2.4 g of $AlCl_3.6H_2$, 50 mg of $KCr(SO_4)_2.12H_2O$ and 26 mg of $NiSO_4.6H_2O$; 100 ml of concentrated hydrochloric acid are added and the solution is autoclaved at 120° C. for 30 minutes.

The pH of the solution is brought to 7.4 by the addition of an aqueous solution of KOH (d=1.38) and the solution is then kept at 120° C. for 45 minutes. 100 ml of a filtered aqueous solution of glycerol (18.4 g) and $K_2HPO_4$ (1.5 g) are then added.

A preculture of the lyophilized strains is prepared in this medium, in a shaked flask at 30° C., and 150 ml of preculture are then introduced into 1.35 l of the same medium in a fermentor kept at between 28° C. and 32° C.; the pH is kept at 7.4 by the addition of NaOH or HCl and the medium is aerated by the introduction of fresh air under a slight pressure.

Culture is continued until about 8 g of biomass per liter are obtained.

b) Production phase

The production medium consists of a solution, in 800 ml of deionized water, of casein hydrolyzate (1.13 g); $MgSO_4.7H_2O$ (50 mg); $MgCl_2.6H_2O$ (85 mg); $CaCl_2.2H_2O$ (27 mg); and lysine (1 g), whose pH has been brought to 7 by the addition of KOH before sterilization and which is mixed with a solution of $K_2HPO_4$ (4 g), sodium hexametaphosphate (250 mg) and glucose (45 g) in 100 ml of deionized water.

150 ml of the broth obtained at the end of the growth phase are introduced into 1.35 l of production medium; during fermentation, the temperature is kept at between 28° C. and 32° C. and the pH is kept at 7; the glucose concentration is of more than 10 g/l and the medium is aerated by the introduction of fresh air under a slight pressure.

c) Isolation of the non-viscous xanthan 4 g of the fermentation broth are mixed at 80° C. with 30 ml of water, and 90 ml of isopropanol are then added; after the mixture has been left to stand, it is filtered and the solid is dried at 55° C. for 15 hours.

Table I shows the weight of xanthan isolated in this way per kilogram of medium, together with the viscosity of the fermentation medium from which it is extracted.

The viscosity measurements were made at 25° C. using a Brookfield model LVT viscometer equipped with a n° 2 or 3 spindle rotating at 30 rpm.

TABLE I

| Production time | Viscosity of the broth (mPa · s) | Weight of xanthan (g/kg) |
| --- | --- | --- |
| 21 h 30 min | 22 | 10.6 |
| 24 h | 32 | 11.8 |
| 26 h 30 min | 52 | 14.25 |
| 29 h | 87 | 14.8 |
| 31 h | 130 | 15.7 |
| 46 h | 5400 | 26.3 |
| 50 h | 7100 | 27.1 | d) Separation of the cells 2 g of the solid obtained according to c) are suspended in 100 ml of water and the mixture is centrifuged at 12,000 g for 30 minutes. The centrifugation residue is separated off and the xanthan is precipitated by the addition of isopropanol to the clear solution.

EXAMPLE 2

In another experiment, after a production time of 24 hours, the viscosity of the broth is 10 mPa.s and the weight of xanthan is 13.75 g/kg of broth; 100 mg/l of sodium hexametaphosphate are then added to the broth. After 40 hours, the viscosity is 20 mPa.s and the weight of xanthan is 20.40 g/kg.

What is claimed is:

1. The strain of *Xanthomonas campestris* deposited in the CNCM under n°I-956.

2. A process of producing conventional xanthan, which comprises cultivating *Xanthomonas campestris* CNCM I-956 in a nutrient medium containing 50 to 500 mg/l of an alkali metal hexametaphosphate and 1 to 15 mg/l of calcium ions.

3. The process according to claim 2 wherein the previous growth phase of the microorganism takes place in a medium containing glycerol as the only carbon source.

4. The process according to claim 2 wherein said alkali metal hexametaphosphate is sodium hexametaphosphate.

5. The process as claimed in claim 3, wherein said alkali metal hexametaphosphate is sodium hexametaphosphate.

6. The process as claimed in claim 2, wherein the nutrient medium initially contains 200 to 300 mg/l of alkali metal hexametaphosphate.

7. The process as claimed in claim 2, wherein the viscosity of the medium is less than 32 mPa.s after a cultivation time of 24 hours.

8. A process of producing non-viscous xanthan, an aqueous solution of which at a concentration of 10 g/l has a viscosity of less than 700 mPa.s at 25° C. which comprises cultivating *Xanthomonas campestris* CNCM I-956 in a nutrient medium containing 50 to 500 mg/l of an alkali metal hexametaphosphate and 1 to 15 mg/l of calcium ions and stopping the culture when the viscosity of the medium increases.

9. The according to claim 8 wherein the previous growth phase of the mirooganism takes place in a medium containing glycerol as the only carbon source.

10. The process as claimed in claim 9, wherein said alkali metal hexametaphosphate is sodium hexametaphosphate.

11. The process according to claim 8 wherein said alkali metal hexametaphosphate is sodium hexametaphosphate.

12. The non-viscous xanthan aqueous solution that has a viscosity of less than 700 mPa.s at a concentration of 10 g/l and a temperature of 25° C., the xanthan in the aqueous solution being made by the process of claim 8.

13. The process as claimed in claim 8, wherein the nutrient medium initially contains 200 to 300 mg/l of alkali metal hexametaphosphate.

14. The non-viscous xanthan aqueous solution that has a viscosity of less than 250 mPa.s at a concentration of 10 g/l and a temperature of 25° C., the xanthan in the aqueous solution being made by the process of claim 8.

15. The non-viscous xanthan, an aqueous solution of which has a viscosity of less than 700 mPa.s at a concentration of 10 g/l and a temperature of 25° C., said xanthan being made by the process of claim 8.

16. A non-viscous xanthan having an average molecular weight of about 6 to $7 \times 10^5$, an aqueous solution of which has a viscosity of less than 700 mPa.s at a concentration of 10 g/l and a temperature of 25° C.

17. The non-viscous xanthan as claimed in claim 16, an aqueous solution of which has a viscosity of less than 250 mPa.s at a concentration of 10 g/l and a temperature of 25° C.

* * * * *